United States Patent [19]
Knight et al.

[11] Patent Number: 5,441,873
[45] Date of Patent: Aug. 15, 1995

[54] APPARATUS FOR MONITORING LIQUIDS

[76] Inventors: Jan H. Knight; Robert H. Knight, both of The Laboratory, 18 Western College Road, Plymouth, England, PL4 7AG

[21] Appl. No.: 204,303
[22] PCT Filed: Sep. 8, 1992
[86] PCT No.: PCT/GB92/01638
§ 371 Date: Mar. 10, 1994
§ 102(e) Date: Mar. 10, 1994
[87] PCT Pub. No.: WO93/05142
PCT Pub. Date: Mar. 18, 1993

[30] Foreign Application Priority Data
Sep. 11, 1991 [GB] United Kingdom ............... 9119382

[51] Int. Cl.6 .................. C12M 1/34; C12Q 1/02; C12Q 1/04
[52] U.S. Cl. ........................ 435/34; 435/29; 435/284; 435/291; 435/808
[58] Field of Search ............... 435/808, 291, 31, 34, 435/4, 29, 284, 8

[56] References Cited

U.S. PATENT DOCUMENTS

| 3,370,175 | 2/1968 | Jordon et al. | 435/291 |
| 3,679,312 | 7/1972 | Mansberg | 435/808 |
| 3,958,938 | 5/1976 | Doonan et al. | 435/291 |
| 4,357,420 | 11/1982 | Bostick et al. | 435/291 |
| 4,385,113 | 5/1983 | Chappelle et al. | 435/291 |

FOREIGN PATENT DOCUMENTS

| 0189599 | 8/1986 | European Pat. Off. |
| 0315944 | 5/1989 | European Pat. Off. |
| 2005018 | 4/1979 | United Kingdom |
| WO85/00890 | 2/1985 | WIPO |

Primary Examiner—Jeffrey E. Russel
Attorney, Agent, or Firm—Nixon & Vanderhye

[57] ABSTRACT

An apparatus for monitoring the presence of toxic substances in liquids is disclosed. The monitoring system is based on the use of luminescence systems such as those produced by luminescent microorganisms. The apparatus comprises a sampling device for obtaining a sample of the liquid, a device for providing a continuous culture of organisms or cells for supplying luminescence reagents and a detection device for detecting light emitted from mixture.

16 Claims, 2 Drawing Sheets

APPARATUS FOR MONITORING LIQUIDS

BACKGROUND OF THE INVENTION

1. Field of the Invention

This invent&on relates to an apparatus and a method for continually monitoring the presence liquids of toxic substances, bacteria or any substance or organism which leads to change in the luminescent output of luminescent organisms or luminescence systems. The method involves adding a substance or substances or organisms capable of emitting light to the liquid and analysing light emitted from the resulting mixture.

2. Discussion of Prior Art

Analysis by emitted light is an effective and rapid method for hygiene monitoring and toxicity testing. Rapid and highly sensitive methods for toxicity testing have been based upon the use of luminescent bacteria, in which a reduction of the light emitted by the bacteria is proportional to the presence of toxic materials in the sample. Such tests are extremely sensitive and quantitative. They are used for example by manufacturers in quality assurance of raw materials and to monitor quality during manufacture. They are used to measure the toxicity of untreated and treated wastewaters and as an alternative to animal testing by the cosmetics industry. Their widespread use is being encouraged in the U.K. by the National Rivers Authority.

A number of commercially available luminescence tests for hygiene and toxicity monitoring are currently available and are either based on the luminescent system of the firefly or that of a number of species of luminescent bacteria. They are all performed manually and individually on previously collected samples. They could not be relied upon to monitor unexpected episodes in which pollutants are deliberately or accidentally discharged into a water course. They could not be used easily to monitor changes in the quality of a liquid in a process plant or in the continual quality control of washing of products. They are severely limited by the number of samples that can be collected and the interval between samples. Using an autosampler could increase the number of samples analysed but the corresponding increased cost in reagents would limit the popularity of such an automated system.

U.S. 4,357,420 discloses a method for the detection of biomarkers from biological fluids using luminescence. This process involves the chromatographic separation of samples of biological fluids in which specific biomarkers may be detected. The method uses individual samples of biological fluids and is unsuitable for the detection of unknown biomarkers.

GB 2005018 discloses a method for detecting a toxic substance by detecting the change in light output from a suspension of luminescent microorganisms in an aqueous liquid. The method is, however, based on the analysis of discrete samples of liquid.

U.S. 4,385,113 teaches the use of a bioluminescent system to assay for the presence of ATP and, hence, microorganisms in an aqueous system.

Bains, in Biotechnology, volume 10, May 1992, pages 515 to 518, describes commercially available sensors and states that since they are not continuous sensors, they have found only limited use.

Previously known systems rely on providing a reservoir of bacterial culture either freshly grown in a closed batch culture system or reconstituted from dried bacterial culture but ensuring in some way that the bacteria do not multiply.

Luminescent bacteria grown in closed culture will exhibit various stages of growth:lag phase, acceleration phase, exponential phase, retardation phase and death phase. Closed batch culture vessels will contain a mixture of microorganisms at various stages of the cell cycle. The number of microorganisms will increase at varying rates during the different phases of growth of a culture and the culture will eventually decline and die. As the number of organisms in the culture increases the environment in which they live changes. Many cellular components, such as ATP, DNA and proteins alter in response to these changes and thus the differences between individuals in their biochemical responses (such as luminescence) will also vary. It is for many of the above reasons that the currently used batch tests are designed to prevent the growth of the fresh or reconstituted dried bacteria.

There is however another way to grow microorganisms and that is in open growth systems where there is a continuous input of growth substrates (medium) and removal of waste products, cells and unused substrate. Parameters such as pH, oxygen, temperature etc. can be monitored during the growth with any changes automatically compensated for, for example by the addition of substances to reduce or increase the pH, change the temperature, oxygen content or other conditions.

In these continuous flow cultures the exponential growth phase is prolonged indefinitely as additions to and removal from the culture take place continuously. Thus the characteristics of the population of microorganisms, and that part of it removed for use, remain constant.

SUMMARY OF THE INVENTION

The present invention provides an apparatus and a method for continuously monitoring ("on-line") the presence of potentially toxic materials in a liquid comprising the use of a continuous culture of luminescent microorganisms which may be fed continually into the on-line system to screen for the presence of potentially toxic material. The apparatus of the present invention allows a stream of liquid such as effluent or river water to be monitored continually and, optionally, automatically.

Accordingly, the present invention provides an apparatus for substantially continuously monitoring for the presence of toxic substances or bacteria in liquids comprising:

(i) sampling means for obtaining a sample of liquid;
(ii) means for providing a continuous culture of organisms or cells for supplying luminescence reagents such that the characteristics of the population of organisms or cells remain substantially constant;
(iii) means for allowing the luminescence reagents to come into contact with at least a portion of the sample to form a mixture; and
(iv) detection means for detecting any light emitted from the mixture.

The luminescence reagents are preferably luminescent microorganisms. The sample may be divided into at least two streams, at least one but not all of said streams remaining untreated by luminescence reagents. The apparatus is preferably adapted to allow for substantially continuous monitoring of the liquid. In a preferred embodiment, the detection means is capable of detecting differences between the light emitted from the mixture and the untreated stream and, for example, comprises a photodetector. The apparatus may further comprise means for carrying out different methods of continuous analysis on the streams and may comprise collection means for collecting untreated streams. The detection means may be capable of communication with the collection means such that portions of samples emitting a predetermined amount of light when treated by the treatment means may be collected untreated (e.g., by collecting at least one untreated stream for concentration by, for example, reverse osmosis is under pressure or by using at least one adsorption column with concentrated sample eluted from columns at preset times ). The sample is preferably obtained as a substantially continuous stream of the liquid. The invention also provides a method for substantially continuously monitoring for the presence of toxic substances or bacteria in liquids comprising:

(i) obtaining a sample of liquid;
(ii) providing a continuous culture of organisms or cells for supplying luminescence reagents such that the characteristics of the population of organisms or cells remain substantially constant;
(iii) allowing the luminescence reagents to come into contact with at least a portion of the sample to form a mixture; and
(iv) detecting any light emitted from the mixture.

The apparatus may also include: means for comparing the light emitted from the mixture with a reference sample; means for setting threshold levels for substances being monitored in order to activate alarms and/or divert untreated samples for collection; means, if required, for extracting on-line, components of luminescent cells or organisms; means, if required, for separating and purifying components extracted from cells or organisms; means, if required, for adding various substances to the mixture and allowing time for reactions to occur; and/or means, if required, for controlling the temperature during the on-line processes.

The term luminescence reagents, as used herein, includes luminescent organisms or cells (both naturally occurring and genetically altered) and the luminescent systems present in these organisms and cells (e.g., photoproteins, luciferins, luciferases) which may be extracted from the organisms and cells in the apparatus in ways well-known to those skilled in the art.

In the present invention luminescent microorganisms or cells are grown in continuous culture. A continuous supply of such luminescent microorganisms or cells will have uniform properties. Luminescent cells with partial luminescent systems may also be grown in continuous culture. Such continuously grown cells or organisms having uniform properties may be supplied to an on-line toxicity monitoring part of the apparatus as discrete samples but are preferably supplied in a substantially continuous manner.

By including on-line extraction and possible purification procedures, the luminescent substances derived from such continuously grown cells or organisms may be extracted from the organisms and used to supply almost any amount of luminescent material to any on-line continual monitoring system. On-line extraction procedures could include chemical methods such as the use of detergents, changes in osmolality, addition of acids, alkalis and hydrolytic or other enzymes. Physical methods of extraction might also be incorporated into a continuous on-line system by, for example, incorporating ultrasonication techniques on-line, e.g., by inserting a probe via a T-piece into the continuous line. The probe is essentially a single transducer which couples energy into a chemical reaction by means of a velocity transformer. Alternatively the continuous line could be passed through a liquid-filled tank with multiple transducers bonded around the base and walls.

If a luminescent microorganism, such as *Noctiluca milaris*, which requires to be fed another microorganism, such as the marine alga Dunaliella, the marine alga can be grown in an adjacent continuous culture system and supplied to the vessel in which the Noctiluca are growing in the same way as media or other substances are provided to the culture system.

An on-line monitoring system supplied with luminescence reagents produced continuously as part of the system (i.e., in a continuous culture) can theoretically run for an indefinite period of time. In practice, however, such a system is more likely to run unattended for between 4-6 weeks when a regular maintenance or check is likely to be carried out.

The present invention with its own continuous supply of luminescence reagents provided by luminescent organisms or cells, or by the on-line extraction and purification of substances from such continuously grown organisms or cells, can provide a relatively inexpensive supply of reagents to a continuously running monitoring system.

While the object of growing continuous cultures of luminescent organisms or cells is to feed an on-line monitoring system, the actual continuous culture part of the system can also be used to supply batches of luminescent material for discrete samples. For this reason, the apparatus may comprise means for tapping discrete samples of culture. These discrete samples may then be used to determine the presence of toxic substances in other liquid samples.

The means for providing a continuous culture preferably comprises a vessel and may be one of a number of commercially available systems which can be removed for cleaning, servicing and sterilizing. The vessel and continuous culture part of the system may, alternatively, comprise a disposable system which might be a plastics (or glass) container into which culture media and other necessary reagents are added. The vessel can be supplied either: (i) containing a starting culture of freeze dried organisms into which culture medium is added; or (ii) with a separate starting culture of organisms (which can be microorganisms or cells) added to the vessel. The culture vessels, reagents, reference and other liquids, may all be supplied in or as disposable vessels. The volume of reference liquid used is equal to the volume of sample analysed (if both lines are running continuously).

The reference liquid, if supplied in a disposable vessel with two compartments could deliver reference liquid from one compartment and receive processed sample and reference liquid into the other. The capacity of the waste compartment would need to be about twice that of the reference compartment. When the waste compartment is detected as full, a valve may be automatically activated shutting off the reference and waste lines and bringing in line a new vessel with reference liquid and waste compartment. Alternatively the waste line may run downstream of the sample line as the luminescent organisms used are marine and non-toxic.

The system is designed to monitor the existence of toxic substances in places where they would not be expected e.g., toxic substances or raw industrial waste in a water supply or river but may also be used where toxic substances are expected. Monitoring wash water used to remove toxic substances from goods or equipment may be carried out allowing their use only when all toxic substances have been removed. Similarly, industrial waste may need to be diluted or made non-toxic before being discharged and this process may be monitored using the present invention. Generally, the invention is applicable to any process which involves the removal or monitoring of toxic substances for quality assurance or for waste disposal. The system may be used with many species of luminescent bacteria such as *Photobacterium phosphoreum* and with other luminescent microorganisms well known to those skilled in the art. These include the dinoflagellates such as Noctiluca and ostracods such as Cypridina and Vargula. In addition luminescent metamorphosed larvae of *Pholas dactylus* may be used. The continuous culture may also be used to provide reagents for the detection of ATP by methods such as that disclosed in U.S. Pat. No. 4,385,113. Thus, the continuous culture of a bacterium such as *Escherischi coli* transfected with a gene coding for a protein involved in a luminescent reaction (such as the luciferase of the firefly used in ATP determinations) may, after on-line manipulations and extraction procedures, be supplied to the on-line monitoring system for the detection of ATP. In addition the continuous culture of luminescent cells derived from bioluminescent organisms such as the mollusc *Pholas dactylus* might also be used to supply the on-line monitoring system.

The method by which the luminescent organisms or cells are used in the system to monitor toxic materials could vary: with *Photobacterium phosphoreum*, which glows continuously, the presence of toxic material leads to a reduction of light. In the presence of other luminescent organisms, such as *Noctiluca milaris* or *Gonyaulax polyeda*, which luminesce on stimulation, conditions under which luminescence is induced can be monitored. Similarly, certain dark mutants of luminescent bacteria can be induced to become luminescent under certain conditions. The ability to grow any luminescent organism or cell, including genetically engineered organisms and cells and dark mutants, can allow for the use of this system in a variety of ways to monitor for the existence of specific substances or to screen for the existence of a wide range of substances.

Chemiluminescent materials either synthesised or derived from natural organisms (such as the photoprotein Pholasin ®, a registered trade mark of Knight Scientific Limited, derived from the bioluminescent mollusc *Pholas dactylus*) may, in addition to the luminescent bacteria and metamorphosed larvae, be used in separate monitoring lines. These substances may be more or less sensitive to specific toxic substances such as heavy metals, pesticides, herbicides, etc. Not all luminescent substances respond in an identical manner to the presence of toxic substances and therefore when running a number of lines, more information becomes available and more useful samples can be collected for further analysis.

The apparatus of the present invention is particularly useful in the monitoring of a continuous stream of liquid, particularly aqueous liquids. The apparatus allows for constant monitoring which cannot be carried out effectively by the present luminescence method involving discrete samples. Sampling by the apparatus may be carried out substantially continually e.g., by removing a continuous stream of liquid from the liquid to be monitored or by removing discrete samples at frequent time intervals. This process is carried out by methods well-known to those skilled in the art preferably over a predetermined period of time to give regular readings for effective monitoring representing an improvement over previous manual methods. The results of monitoring the liquid may be presented on a display (of a type well-known in the art) or stored in a memory for subsequent retrieval.

The apparatus comprises detection means that may detect the difference in intensity between light emitted by a mixture of luminescence reagents with non-toxic and/or foreign bacteria-free liquid and the mixture of luminescence reagents with the sample to be monitored. Hence in a preferred embodiment of the invention the sample is split into at least two lines and luminescence reagents are fed continually by treatment means into the two lines of liquid. The reference line will consist of non-toxic and/or foreign bacteria-free liquid (such as relatively pure water, non-toxic aqueous solutions, brine, or another relatively pure solvent). The other line will contain the liquid to be monitored. After allowing the mixture to be monitored sufficient time to undergo a possible change in the intensity of emitted light (e.g., by passage through a given length of tube in the apparatus) both lines are measured for luminescence by detecting the light emitted from each stream.

The sample of liquid to be monitored may be split into more than two lines and each line monitored for different parameters. Hence, besides reference lines and lines for testing by addition of luminescence reagents the sample may be split into additional lines. These may be tested continuously ("on-line") for parameters such as temperature, pH, dissolved oxygen, redox potential, etc. In this way more specific information may be derived during the on-line analysis. This further testing may conveniently be carried out by analysis of emitted light using luminescent materials such as Pholasin ® or in one of a number of ways well known to those skilled in the art such as colorimetric, ultra-violet or fluorescence methods. Each of these extra analytical methods may constitute a single module which may be added to the apparatus at any time to provide the apparatus with a further analytical technique.

The apparatus may also comprise means for collecting untreated portions of the sample. This may consist of an additional line of the liquid to be monitored (untreated with luminescence reagents) which travels a longer distance than the treated line or lines before leaving the apparatus. This may be effected by passing the untreated line through a loop or coil. Hence, there is a delay before the liquid in the untreated line is discarded. If, during the monitoring of the sample, toxic substances or bacteria are detected above a given threshold (which may be determined in advance), then the system will activate the means for collecting untreated sample such as the switching of a valve to allow the collection of discrete portions of the sample. Portions may be collected, therefore, of the liquid giving the specified toxicity reading. The apparatus may include controlling means (e.g., a computer interfaced to a neural network board) to carry out some or all of the operations of the apparatus automatically, to coordinate information derived from the various monitoring lines and be able to 'remember' what combination of readings would under some circumstances be considered normal and under others, abnormal. The apparatus may also comprise indicating means such as an alarm to alert an operator.

The collected portions of liquid (the volumes of which may be predetermined by the operator during the set-up of the system) may be collected into containers. Preferably the containers may be sealed and marked with the date and time of collection within the apparatus. The containers may be in the form of sacks made from plastics material and may be dispensed from a roll. The containers may be capable of being securely sealed such that any tampering with the sample is evident from the container enabling the samples to be used for further analysis for diagnostic purposes or for use in the prosecution of offences.

The mechanism of detection of light may be from a number of photodetectors, such as photomultiplier tubes or solid state detectors. The sample may be contained within a flow cell which is continuous with the tubing of the on-line system. The flow cell can be made from tubing coiled many times into a helix. The volume of the flow cell is determined by the length of the tubing in the helix and of the internal diameter of the tubing. The flow cell is preferably positioned near to the photodetector. Light from the sample or sample lines in one or more flow cells and the reference flow cells is detected either by one photodetector or a series of photodetectors. If one photodetector is used then light from each flow cell is detected in turn. This can be achieved in a number of ways (e.g., by the photodetector to be shielded from light by a rotating shield which contains an aperture). The shield can be fitted as a collar around the photodetector. As the collar rotates, light from each flow cell is detected in turn by the photodetector. Other arrangements can be made, depending upon the positioning of the flow cells relative to the photodetector.

The duration of photodetection from each flow cell is determined by the rate at which the shield revolves, the size of the aperture and the distance between each flow cell. Such parameters will determine for what length of time each flow cell is exposed to the photodetector. Similarly the sensitivity of detection can be changed by changing the size and dimensions of the aperture in the shield and the rate of rotation of the shield. Both streams go to waste after measurement and, since the luminescence systems are generally both harmless and naturally occurring (e.g., bioluminescent microorganisms which live naturally in sea water but will not live in fresh water), there is no possibility that the process of monitoring for pollutants will actually lead to pollution itself or to the growth of microorganisms in the waste water. Similarly, the naturally occurring luminescence system components (such as firefly luciferin and firefly luciferase) will not lead to unwanted pollution.

The apparatus of the present invention may also include means for monitoring the amount of toxic substances or bacteria in samples which are relatively dilute (e.g., too dilute to be detected by the analysis of emitted light method employed in the present invention). Hence the apparatus of the present invention may include means for the diversion of a sample (by means of a valve, for example) of a predetermined volume of liquid. The sample may be diverted as desired such as after a predetermined time of monitoring samples when no toxic substances or bacteria have been detected. The predetermined volume of liquid is then concentrated in the apparatus by means for concentrating the sample e.g., by passage through one or a series of reverse osmosis filters under pressure or through one or more adsorption columns, elution from which may be performed at set intervals. The volume of fluid concentrated can be determined by the rate of flow in the on-line system and set interval of elution. The concentrated sample may then be analysed for the intensity of emitted light in the presence of luminescent bacteria or luminescence system components either by diversion to the detection means of the apparatus or by a separate detecting means.

The whole on-line system may be housed within a single container (e.g., a cabinet) in which are contained all the necessary means for supplying media, collecting waste, growing all organisms and monitoring the liquid, including the photodetector(s), pumps and controller. The system can also be arranged so that any part of the system, such as the means for providing a continuous culture occupies a different location from the remainder of the apparatus. In addition, the system may have sufficient capacity (e.g., a large enough continuous culture and/or processing ability) to supply more than one line.

All or part of the tubing in the system, including the means for providing a continuous culture and the flow cell for the detection means can be made from a tubing such as Teflon ® tubing which can be disposed of and replaced from time to time with new tubing. To increase further the capacity of the system, either additional continuous culture devices can be inserted in the monitoring system or a larger continuous culture system used. The rate of growth of bacteria in the system may be monitored by luminescence detection and the system may provide a means of diluting the cultures.

The apparatus may provide means for supplying freeze dried luminescent bacteria such as in disposable containers which when reconstituted with appropriate media can be inserted into the system from which the reconstituted bacteria may be continuously dispensed to the continuous culture and/or to the sample and reference lines to supplement the continuous culture. Such an arrangement may be more suitable in portable systems to be used in remote places and may allow the use of a flask of reconstituted luminescent bacteria in place of the continuous culture vessel for converting the system into a quick portable system for remote testing. However systems to be used in the field may include the continuous culture of bacteria since the monitoring system may be transported in a mobile laboratory. Energy required for the portable system may be provided by a number of sources such as battery, solar power and generators run by petrol or gas.

BRIEF DESCRIPTION OF THE DRAWINGS

A preferred embodiment of the present invention will now be described with reference to the accompanying figures.

DETAILED DESCRIPTION OF PREFERRED EMBODIMENTS

Figure 1:
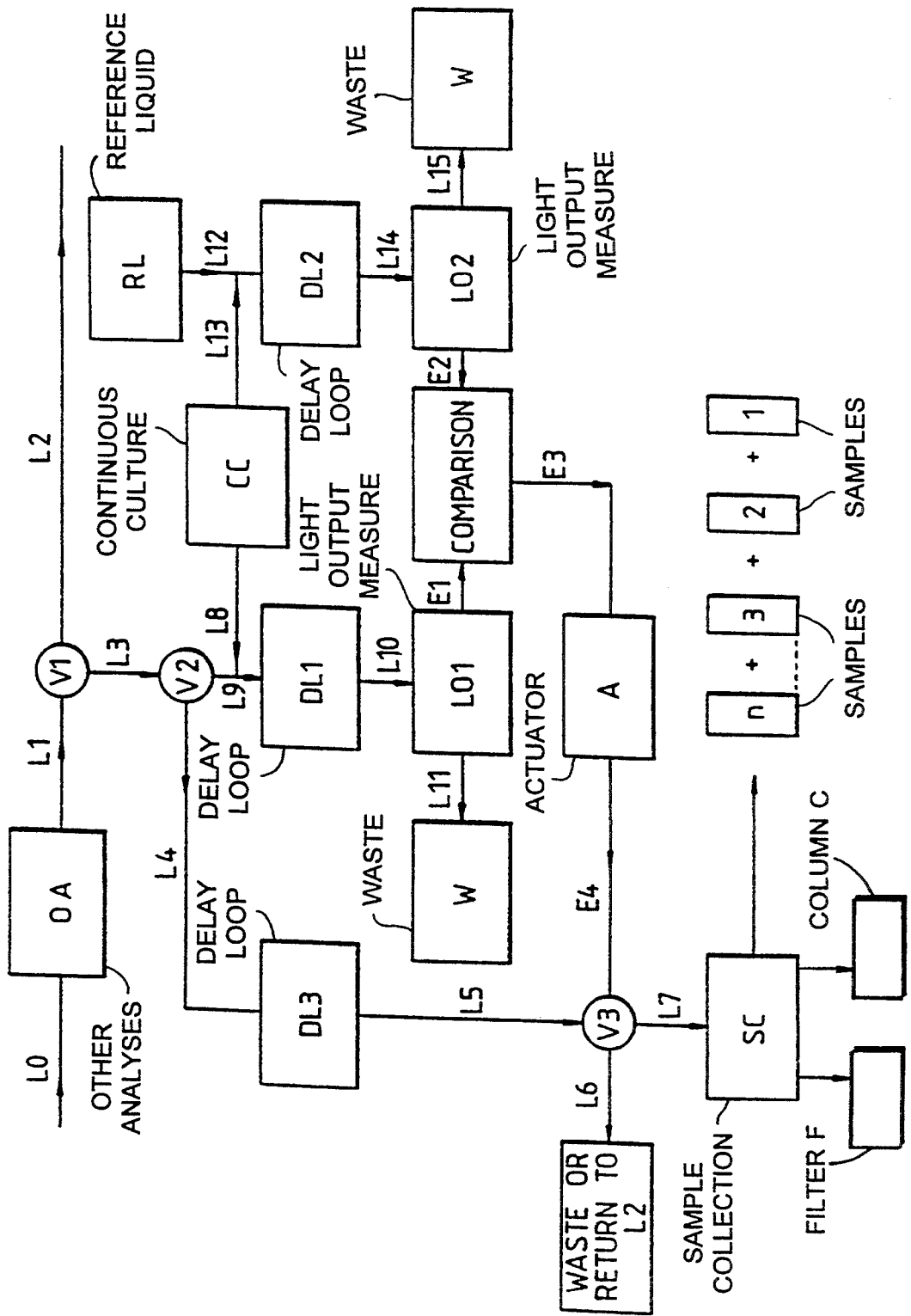
FIG. 1 shows schematically the arrangement of the apparatus of the present invention when using luminescent bacteria.

With reference to FIG. 1, the material to be analysed passes along line L0. Other analyses, OA, may be carried out on the material before passing along line L1. Valve V1 diverts part of the flow along line L3 while the main flow continues along line L2. The flow may be split into further streams before or after V1 for analysis by methods other than using luminescent bacteria (not shown). Valve V2 interrupts the flow in L3 and diverts some of the flow to line L4 while the rest goes through line L9. Continuous culture CC provides luminescent bacteria L8 or extracted luminescent reagent which are mixed with the flow in L9. The mixture spends as much time in delay loop DL1 as is necessary for the substances present in the material to be analysed to have their effect on the bacteria, and hence on the bacterial luminescence and then passes along line L10. The light output LO1 from the bacteria is measured and the measured liquid discarded to waste W via line L11 (after suitable sterilisation treatment where necessary).

A reference liquid RL, known not to contain substances that would affect the luminescent bacteria passes into L12 where it is met by a flow of bacteria from CC along L13. After passing through delay loop DL2 and along line L14, the light output LO2 is measured and the liquid sent to waste W, after suitable sterilisation where necessary, along L15. The two measurements of light output from the sample and the reference material are sent along electronic lines E1 and E2 respectively. A comparison is made between the two measurements and for certain predetermined differences a signal is sent along E3 to an actuator, A, that itself sends a signal along E4 that causes valve V3 to be activated to divert the flow from L5 along L6 to waste or return to L2 or along L7 to a sample collection device SC in which discrete, time- and date- stamped samples (1, 2, 3, . . . n) are collected and sealed or sample concentration in reverse osmosis filter F or in absorption column C. The time of passage between V2 and V3 of the sample diverted through delay loop DL3 may be made equal to the time taken by the analysed sample between passing through V2 and leading to the activation of V3.

LO1 and LO2 may derive from a single photodetector by alternately switching the aperture of the device between the sample stream or analyte and the reference. By the same means a single photodetector may be used to monitor n different samples or analytes by arranging 2n apertures to be presented to the photodetector, each pair presenting the sample or analyte followed by the specific reference for each sample or analyte.

Figure 2:
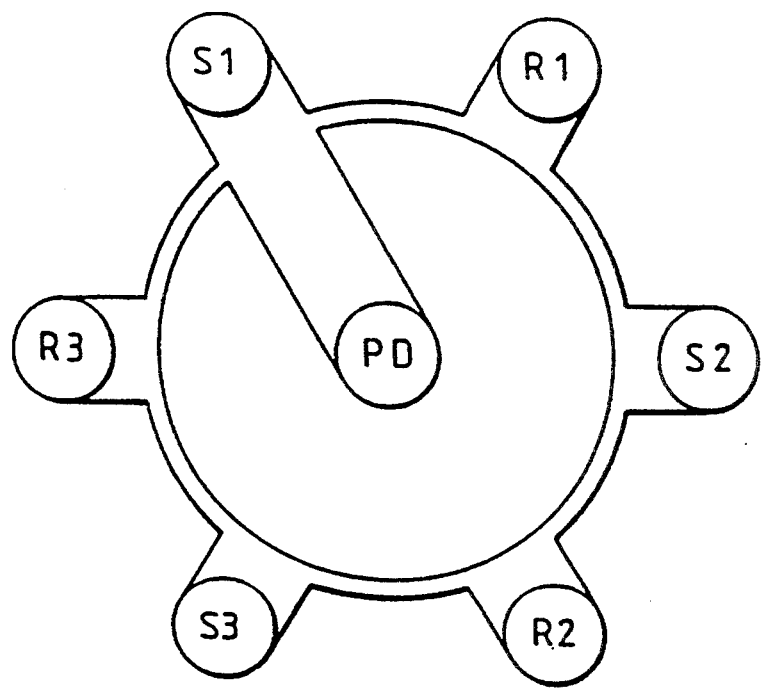
FIG. 2 shows a possible arrangement of flow cells and photodetector.

With reference to FIG. 2, for three sample streams or analytes S1, S2, S3 the aperture may be made to move through 60° at each switching and the sample stream or analyte flow cells and their corresponding reference liquids R1, R2, R3 are arranged at 60° intervals around photodetector PD. An arrangement for light insulation between all the sample flow cells and all the reference flow cells is incorporated into the system. The flow cells may be arranged peripherally to the detector in a circular manner beneath the detector depending on the positioning of the detector. Alternatively for a photodetector, the sensitivity of which was not constant over 360°, the photodetector together with its aperture is made to move in, for example, 60° steps. Movement of the aperture brings each flow cell, in turn, into visual contact with photodetector PD.

Figure 3:
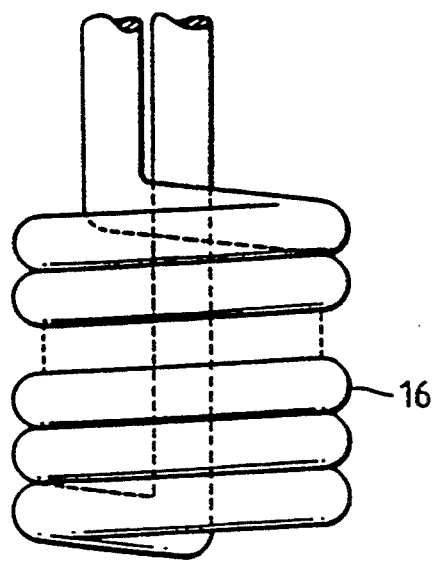
FIG. 3 shows a flow cell which may be used in the present invention.

With reference to FIG. 3, a flow cell for on-line monitors 16 is made from plastics tubing (e.g., Teflon®) tubing) and has an internal diameter of less than 1 mm. Flow cells with larger tubing may be constructed in a similar way. Flow cell 16 may be kept in a uniform position relative to the photodetector by placing the cell within a transparent cuvette.

The following examples illustrate continuous cultures which may be used in the invention but are not intended to limit its scope in any way.

EXAMPLE OF CONTINUOUS CULTURE

The luminescent bacterium, *Photobacterium phosphoreum*, was grown in continuous culture in the following media:

| | | |
|---|---|---|
| 1 - peptone | 5 | g |
| yeast extract | 3 | g |
| glycerol | 3 | ml |
| NaCl | 17.5 | g |
| KCl | 1.3 | g |
| $CaCl_2.2H_2O$ | 2.2 | g |
| distilled water | 1 liter | pH 7.8 |
| 2 - peptone | 5 | g |
| yeast extract | 3 | g |
| glycerol | 3 | ml |
| seawater | 1 liter | pH 6.5 |
| 3 - peptone | 5 | g |
| yeast extract | 5 | g |
| glycerol | 3 | ml |
| NaCl | 30 | g |
| $Na_2HPO_4.2H_2O$ | 6 | g |
| $KH_2PO_4$ | 1 | g |
| distilled water | 1 liter | pH 6.5 |

840ml of the culture was maintained at a temperature of 25° C. and at pH 6.5 with agitation and aeration at 500–600 ml/min. Antifoam agents may, optionally, be added to control frothing. A steady growth rate was achieved at 200 μl/min which was approximately 5% of maximum growth rate. The specific growth rate can be changed in order to satisfy different conditions but changes to the specific growth rate will result in corresponding changes to the amount of nutrients added.

We claim:

1. Apparatus for substantially continuously monitoring for the presence of toxic substances or bacteria in liquids comprising: (i) sampling means for obtaining a sample liquid; (ii) means for providing a continuous culture organisms or cells for supplying luminescence reagents such that the characteristics of the population of organisms or cells remain substantially constant; (iii) means for allowing the luminescence reagents to come into contact with at least a portion of the sample to form a mixture; and (iv) detection means for detecting any light emitted from the mixture.

2. Apparatus as claimed in claim 1, wherein the luminescence reagents are luminescent microorganisms.

3. Apparatus as claimed in claim 1, wherein the sample comprises at least two streams, at least one but not all of said at least two streams remaining untreated by luminescence reagents.

4. Apparatus as claimed in claim 1, wherein the detection means is capable of detecting differences between the light emitted from the mixture and a reference sample.

5. Apparatus as claimed in claim 1, wherein the detection means comprises a photodetector.

6. Apparatus as claimed in claim 3, further comprising means for carrying out different methods of continuous analysis on the streams.

7. Apparatus as claimed in claim 3, further comprising collection means for collecting untreated streams.

8. Apparatus as claimed in claim 7, wherein the detection means is capable of communication with the collection means such that portions of samples may be collected untreated.

9. Apparatus as claimed in claim 6, wherein said sampling means includes means for collecting at least one untreated stream for concentration.

10. Apparatus as claimed in claim 9, wherein said means for collecting includes reverse osmosis under pressure concentration.

11. Apparatus as claimed in claim 9, wherein said means for collecting comprises at least one adsorption column with concentrated sample elution at present times.

12. Apparatus as claimed in claim 1, said means for providing comprising means for extracting the luminescence reagents from the organisms or cells on-line.

13. Apparatus as claimed in claim 12, wherein the means for extracting the luminescence reagents includes one of sonication, changing osmolality of a carrier medium and addition of chemical reagents.

14. Apparatus as claimed in claim 13, wherein said means for extracting comprises the addition of chemical reagents and said addition of chemical reagents comprises the addition of at least one of detergents, acids, bases and enzymes.

15. Apparatus as claimed in claim 1, wherein said sample comprises a substantially continuous stream of the liquid.

16. A method for substantially continuously monitoring for the presence of toxic substances or bacteria in liquids comprising:
 (i) obtaining a sample of liquid;
 (ii) providing a continuous culture of organisms or cells for supplying luminescence reagents such that the characteristics of the population of organisms or cells remain substantially constant;
 (iii) allowing the luminescence reagents to come into contact with at least a portion of the sample to form a mixture; and
 (iv) detecting any light emitted from the mixture.

* * * * *